(12) United States Patent
Cuzzato et al.

(10) Patent No.: US 6,791,001 B2
(45) Date of Patent: Sep. 14, 2004

(54) PROCESS TO OBTAIN CFC 113A FROM CFC 113

(75) Inventors: Paolo Cuzzato, Treviso (IT); Letanzio Bragante, Padua (IT)

(73) Assignee: Ausimont S.p.A., Milan (IT)

( * ) Notice: Subject to any disclaimer, the term of this patent is extended or adjusted under 35 U.S.C. 154(b) by 0 days.

(21) Appl. No.: 10/072,873

(22) Filed: Feb. 12, 2002

(65) Prior Publication Data
US 2002/0151755 A1 Oct. 17, 2002

(30) Foreign Application Priority Data
Feb. 13, 2001 (IT) .................................. MI2001A0287

(51) Int. Cl.$^7$ .............................................. C07C 21/00
(52) U.S. Cl. ...................................................... 570/151
(58) Field of Search ........................................ 570/151

(56) References Cited

U.S. PATENT DOCUMENTS

| | | | |
|---|---|---|---|
| 2,598,411 A | * | 5/1952 | Miller et al. |
| 5,243,106 A | * | 9/1993 | Manzer et al. ............... 570/166 |
| 5,414,164 A | | 5/1995 | Brown et al. |
| 5,672,785 A | | 9/1997 | Morikawa et al. |
| 5,679,613 A | | 10/1997 | Swidersky et al. |

FOREIGN PATENT DOCUMENTS

| | | | |
|---|---|---|---|
| EP | 0 366 404 A1 | | 5/1990 |
| EP | 0 366 404 | * | 5/1990 |
| EP | 0 537 759 A2 | | 4/1993 |
| EP | 0 537 759 | * | 4/1993 |
| EP | 0 879 790 A1 | | 11/1998 |

OTHER PUBLICATIONS

CA:113:61673 abs of Applied Catalysis by Blanchard et al 59(1) pp 123–128 1990.*
Applied Catalysis by Blanchard et al 59 pp123–128 1990.*
Journal of Fluorine Chemistry by Bozorgzadeh et al 107pp45–52 2001.*
Journal of Fluorine Chemistry by Bozorgzadeh et al 112 pp 225–232 2001.*
Patent Abstract; XP–002198323; JP 2989922; Dec. 13, 1999.
Blanchard, M. et al. "Heterogeneous Catalytic Reactions of Chlorofluorocarbons", Applied Catalysis, 1990; 59:123–128.
Bozorgzadeh, H. et al. "Conversion of 1,1,2–trichlorotrifluoroethane to 1,1,1–trichlorotrifluoroethane, and 1,1–dichlorotetrafluoroethane over aluminium–based catalysts", Journal of Fluorine Chemistry, 2001; 107:45–52.
Bozorgzadeh, H. et al. "The behaviour of chlorofluoroethanes on β–aluminium(III) fluoride: a[$^{36}$Cl] radiotracer study", J. of Fluorine Chemistry, 2001; 112:225–232.

* cited by examiner

Primary Examiner—Jean F. Vollano
(74) Attorney, Agent, or Firm—Commolly Bove Lodge & Hutz LLP

(57) ABSTRACT

A process in gaseous phase to obtain CFC 113$a$ starting from CFC 113, wherein CFC 113, optionally diluted with a gas inert under the reaction conditions, is let flow on a catalyst formed by aluminum fluoride.

18 Claims, No Drawings

PROCESS TO OBTAIN CFC 113A FROM CFC 113

The present invention relates to a process which uses 1,1,2-trichloro-1,2,2-trifluoroethane $CCl_2F$-$CClF_2$ (CFC-113 or symmetric isomer of 113) to obtain 1,1,1-trichloro-2,2,2-trifluoroethane $CCl_3$-$CF_3$ (CFC 113a or asymmetric isomer of 113) with very high conversions.

It is well known that CFC-113 is a compound whose use is regulated by the Montreal Protocol and therefore its dispersion in the environment is banned. It is known that for eliminating CFC 113, efficient and not dangerous for the environment methods are to be available. The simplest way for its disposal is generally the combustion. However it is to be made in special ovens able to resist the corrosive action of its decomposition products, in particular HF and HCl and besides equipped with disposal systems of said acids. Said process has therefore the drawback to require expensive plants without obtaining any economic advantage.

A method is therefore desirable which allows the reuse of 113, for example by its isomerization to CFC 113a.

CFC-113a is indeed a product of industrial interest and it is used to prepare various compounds, such as for example trifluoroacetic acid and its derivatives, or halogenated hydrocarbons having 4 carbon atoms, or compounds having an insecticidal activity such as cyhalotrin and tefluthrin etc.

In the prior art processes for the synthesis of CFC 113a starting from CFC 113 are described. U.S. Pat. No. 5,414,164 describes the synthesis of CFC 113a by chlorination of a derivative of trifluoroethane of formula $CF_3$-$CH_xCl_y$, wherein x is an integer in the range 1–3 and y=3–x. In this patent it is stated that the isomerization of CFC 113 to CFC 113a by the methods known in the prior art is not industrially feasible, since the conversions and the selectivity are very low and the products are difficult to be separated and undesired by-products form. In fact the separation of CFC 113a from CFC 113 has not yet been solved in the prior art since it is extremely difficult.

In U.S. Pat. No. 5,672,785 it is described the synthesis of CFC 114a, 1,1,1,2-tetrafluoro-2,2-dichloroethane $CF_3$-$CFCl_2$, starting from CFC 113 which is subjected to isomerization and disproportionation at a temperature in the range 50°–550° C., in the presence of oxygen or chlorine, using as catalyst an halide or an oxide containing at least a metal selected from Al, Cr, Fe, Ni, Co or from alkaline-earth metals. As examples of halides, $AlCl_3$ and $CrCl_3$ are in particular mentioned. The reaction, which can take place both in liquid and in gaseous phase, leads to obtain a mixture comprising CFC 113, CFC 113a, CFC 114 and CFC 114a, which according to the process described in the patent is not isolated but directly reacted with HF to give the final product. From the Tables of the Examples of this patent we deduce that the conversion of the isomerization reaction is not satisfactory, and that in the final gas mixture, together with CFC 114a, there are significant amounts of CFC 113. If one wanted to separate 113a from 113 from this mixture, one would meet the above problems.

U.S. Pat. 5,679,613 describes a process to prepare compounds of formula $CF_3$-$CCl_2X$ wherein X=Cl, F, and therefore also CFC 113a (X=Cl), starting from CFC 113 in the presence of $AlCl_3$ activated by a metal halide selected from $AlCl_3$, $FeCl_3$ or by a salt of formula $NaF.nHF$ (with n in the range 0–2) or AgCl and $FeCl_3$. According to this patent (see the Examples) in the reactor together with the starting compound, $AlCl_3$ and the metal salt are added and the catalyst is activated by mixing the substances at a temperature in the range 10°–30° C. for a time ranging from 1 to 10 hours. The ratio between the weight of the catalyst and of CFC 113 ranges from about 10% to about 90%. When the activation phase is ended, the heterogeneous liquid mixture is heated to 70°–95° C. to convert CFC 113 into CFC 113a. The Examples show that in the process of the patent the CFC 113 conversion is high but that amounts of by-products form in the range from about 8% to about 15%. At the end of the reaction the mixture of the reactants with the products is evaporated; the latter are separated and isolated by distillation, and the catalyst, which can be reused, is recovered. This process has the drawback that it can be carried out only in a discontinuous way. Another drawback is that to use a high ratio between the weight of catalyst and of CFC 113. Besides the separation of the reactants and the catalyst recovery are difficult.

The need was therefore felt of a process to obtain CFC 113a starting from CFC 113 feasible in a continuous way, with substantially quantitative conversions, considering, as regards the catalyst, the use thereof in reduced amounts, an easy separation from the reaction products and its complete recovery after the use, said process having besides the characteristic to obtain CFC 113a from the reaction mixture without having to carry out the separation from 113, which, as said, represents the drawback of the processes of the prior art.

It has been unexpectedly and surprisingly found by the Applicant that the above technical problem can be solved by the process described herein.

An object of the present invention is a process in gaseous phase to obtain CFC 113a starting from CFC 113, wherein CFC 113 in gaseous phase, optionally diluted with a gas inert under the reaction conditions, is let flow on a catalyst formed by aluminum fluoride in a fixed or fluidized bed.

Optionally in the process of the invention CFC 113 can be used in admixture with CFC 113a.

Small amounts of other CFCs can be present, generally in a total percentage not higher than 1% by weight.

The preparation on an industrial scale of the aluminum fluoride is carried out by fluorination of the aluminum oxide (alumina) with anhydrous hydrofluoric acid (HF). The introduced fluorine amount generally corresponds to 95% by weight or more.

The alumina fluorination with anhydrous HF to obtain $AlF_3$ is well known in the prior art and it is for example described in FR 1,383,927. The aluminum fluoride obtained according to this patent is mainly formed by gamma phase.

Preferably the starting alumina is under a hydrated form and has the crystalline structure of the bohemite or the pseudobohemite.

Optionally the alumina can contain silicon oxide (silica) in an amount in the range 1–10% by weight.

Said aluminas are commercially available for example with the trademarks Condea Siral® and Condea Pural® (without silica).

As fluorinating agent to obtain $AlF_3$ anhydrous hydrofluoric acid is used.

If in the process of the invention the catalyst in fluidized bed is used, as crude material to prepare the catalyst, an alumina having a suitable granulometry for this use is employed.

The $AlF_3$ preparation starting from alumina containing silicon oxide is described in patent application EP 879,790 in the name of the Applicant.

The fed CFC 113 amount, expressed as weight ratio between CFC 113/(catalyst×hour), is in the range 0.5–1.5.

The reactant can be fed at the pure state or diluted with a gas inert under the reaction conditions, for example helium or nitrogen.

The reaction temperature is in the range 50° C.–280° C., preferably 100° C.–200° C., still more preferably 100° C.–160° C.

The pressure is not critical and it is possible to operate at pressures comprised between the atmospheric one and up to 10 bar ($10^6$ Pa).

By using the process according to the present invention, variable amounts of the following by-products are formed: dichlorotetrafluoroethane (CFC 114 and CFC 114a), CFC 115 (monochloropentafluoroethane), CFC 111 (pentachloromonofluoroethane) and tetrachlorodifluoroethane (CFC 112 and CFC 112a).

The separation of these by-products from CFC 113a is simpole, since they have very different boiling points. Besides, these compounds can be used as intermediates in synthesis processes.

The obtained CFC 113a has a high purity degree since the residual CFC 113 is lower than 1% by weight based on CFC 113a+CFC 113 present in the reacted mixture, and it is lower than or equal to 0.9% by weight in the preferred temperature range from 100° C. to 160° C. Some Examples follow with illustrative purposes but not limitative of the present invention.

EXAMPLES

In the Examples the used catalyst is formed by aluminum fluoride obtained by fluorination of a hydrated alumina under the form of bohemite containing 1.5% by weight of silica, calculated on the anhydrous product, commercialized by the firm Condea Chemie with the trademark SIRAL® 1,5.

The catalyst preparation is carried out as described in Example 1 of the European patent application No. 879,790 in the name of the Applicant.

370 g of said alumina are transferred into an Inconel 600® tubular reactor having a 50 mm diameter, equipped with electric heating and of a porous septum at the base. The alumina is fluorinated at the temperature of 360° C. for 30 hours using an air/HF mixture. Under stationary conditions the mixture composition is formed by 0.85 moles/h of HF and by 4 moles/h of air.

At the end the reactor is cooled in an air flow. About 510 g of $AlF_3$ are recovered having the following properties: surface area (SA)=34.5 $m^2$/g; pore volume Pv=0.26 $cm^3$/g, crystalline structure: $\gamma$-$AlF_3$ with impurities of $\alpha$-$AlF_3$.

3.26 g of catalyst are transferred in an Inconel® 600 tubular reactor and shortly fluorinated with anhydrous HF at 300° C. to remove possible traces of absorbed water. The reactor is then brought to the working temperature in a helium flow and then, maintaining the flow of the inert gas, the desired amount of CFC-113 is fed, having a titre of 99.5% by weight, the remaining part being formed by CFC-114. The CFC 113 has an isomeric purity higher than 99% by weight, therefore it contains less than 1% by weight of CFC 113a.

Example 1

A mixture formed by about 28 ml/min of helium and 4 ml/–min of CFC 113 is fed to the reactor at the temperature of 107° C.

The gases flowing out from the reactor are washed with water to remove possible traces of acidity, dried and analyzed by GLC using a thermoconductivity detector.

In Table 1 the percentages by weight are reported of the components of the mixture of the reacted gases, the ratio between 113 and 113+113a in the final mixture, and the selectivity (ratio between 113+113a in the reacted mixture and the fed 113 (mixture of isomers)).

In the Table, by CFC 114, the mixture of $C_2Cl_2F_4$ isomers, by CFC 112, the mixture of $C_2Cl_4F_2$ isomers and by "Others" the minor components, mainly CFC 111 and CFC 115, is indicated.

From the data of the Table it appears that the conversion of CFC 113 is very high, since the residual non isomerized CFC 113 is equal to 0.76% by weight of the gaseous mixture and it is equal to 0.9% by weight of the sum (CFC 113a+ residual CFC 113). The selectivity is 82.5%.

Example 2

One proceeds as in Example 1 but at the reaction temperature of 118° C.

From the data in the Table it is shown that the conversion of CFC 113 is very high, since the residual non isomerized CFC 113 is in an amount equal to 0.36% by weight of the gaseous mixture and to 0.4% by weight of the sum (residual CFC 113+CFC 113a). The selectivity is 85%.

Example 3

One proceeds as in Example 1 but at the reaction temperature of 131° C.

From the data in the Table it is shown that the conversion of CFC 113 is very high, since the residual non isomerized CFC 113 is in an amount equal to 0.35% by weight of the gaseous mixture and to 0.4% by weight of the sum (residual CFC 113+CFC 113a). The selectivity is 85.1%.

Example 4

One proceeds as in Example 1 but at the reaction temperature of 153° C.

From the data in the Table it appears that the conversion of CFC 113 is very high, since the residual non isomerized CFC 113 is in an amount equal to 0.59% by weight of the gaseous mixture and to 0.7% by weight of the sum (residual CFC 113+CFC 113a). The selectivity is 83.1%.

Example 5

One proceeds as in Example 1 but at the reaction temperature of 183° C.

From the data in the Table it appears that the conversion of CFC 113 is very high, since the residual non isomerized 113 is in an amount equal to 0.97% by weight of the gaseous mixture and to 1.2% by weight of the sum (residual CFC 113+CFC 113a). The selectivity is 78.7%.

Comments to the Table

With the flow-rates of reacting gases used in the Examples, there is an optimal temperature range between 100° and 160° C. Over 160° C. the selectivity decreases, even if it keeps on acceptable values; under 100° C. the fraction of unconverted 113 increases.

TABLE 1

% by weight of the components of the reacted gaseous mixture and % CFC 113/CFC 113 + CFC 113a, selectivity of the reaction at the temperatures of 107° C., 118° C., 131° C., 153° C. and 183° C.

|  | 107° C. (Ex. 1) | 118° C. (Ex. 2) | 131° C. (Ex. 3) | 153° C. (Ex. 4) | 183° C. (Ex. 5) |
| --- | --- | --- | --- | --- | --- |
| CFC 114 | 10.14 | 9.01 | 8.76 | 9.91 | 11.72 |
| CFC 113 | 0.76 | 0.36 | 0.35 | 0.59 | 0.97 |
| CFC 113a | 81.75 | 84.67 | 84.73 | 82.53 | 77.73 |
| CFC 112 | 5.84 | 4.52 | 4.01 | 4.66 | 5.63 |
| Others | 1.52 | 1.44 | 2.15 | 2.31 | 3.95 |
| 113/113 + 113a | 0.9 | 0.4 | 0.4 | 0.7 | 1.2 |
| Selectivity | 82.5 | 85.0 | 85.1 | 83.1 | 78.7 |

What is claimed is:

1. A process in gaseous phase to obtain CEC 113a starting from CFC 113, wherein CFC 113, optionally diluted with a gas inert under reaction conditions, is let flow on a catalyst consisting of aluminum fluoride in a fixed or fluidized bed at a reaction temperature of from 50° C. to 280° C. wherein the content of residual CFC-113 in the obtained CFC-113a in the final reaction mixture is lower than 1% by weight based on CFC-113a and CFC-113 present in the mixture.

2. A process according to claim 1, wherein CFC 113 is used in admixture with CFC 113a.

3. A process according to claim 1, wherein the fed CFC 113 amount, expressed as weight ratio between CFC 113/ (catalyst x hour), is in the range 0.5–1.5.

4. A process according to claim 1, wherein the aluminum fluoride is obtained by fluorinating an aluminum oxide with anhydrous hydrogen fluoride so that the introduced fluorine amount corresponds to 95% by weight or more.

5. A process according to claim 4, wherein the reaction temperature is at least 100° C.

6. A process according to claim 5, wherein the reaction temperature is in the range of 100° C.–160° C.

7. A process in gaseous phase to obtain CFC 113a from CFC 113, wherein CFC 113, optionally diluted with a gas inert under reaction conditions, is let flow on a catalyst consisting of aluminum fluoride in a fixed or fluidized bed at a reaction temperature of from 50° C. to 183° C., wherein the content of CFC-113a in the final reaction mixture is 77.73% to 84.73% by weight.

8. A process according to claim 7, wherein CFC 113 is used in admixture with CFC 113a.

9. A process according to claim 7, wherein the fed CFC 113 amount, expressed as weight ratio between CFC 113/ (catalyst x hour), is in the range 0.5–1.5.

10. A process according to claim 7, wherein the aluminum fluoride is obtained by fluorinating an aluminum oxide with anhydrous hydrogen fluoride so that the introduced fluorine amount corresponds to 95% by weight or more.

11. A process according to claim 10, wherein the reaction temperature is at least 100° C.

12. A process according to claim 11, wherein the reaction temperature is in the range 100° C. –160° C.

13. A process according to claim 7, wherein the content of residual CFC-113 in the obtained CFC-113a in the final reaction mixture is lower than 1% by weight based on CFC-113a and CFC-113 present in the mixture.

14. A process according to claim 7, wherein the content of CFC-113 in the final reaction mixture is from 0.35% by weight to 0.97% by weight.

15. A process in gaseous phase to obtain CFC 113a starting from CFC 113, wherein CFC 113, optionally diluted with a gas inert under reaction conditions, is let flow on a catalyst consisting of aluminum fluoride in a fixed or fluidized bed at a reaction temperature of from 100° C. to 160° C., wherein the content of residual CFC-113 in the obtained CFC-113a in the final reaction mixture is less than or equal to 0.9% by weight based on CFC-113a and CFC-113 present in the mixture.

16. A process according to claim 15, wherein CEC 113 is used in admixture with CFC 113a.

17. A process according to claim 15, wherein the fed CFC 113 amount, expressed as weight ratio between CFC 113/ (catalyst x hour), is in the range 0.5–1.5.

18. A process according to claim 15, wherein the aluminum fluoride is obtained fluorinating an aluminum oxide with anhydrous hydrogen fluoride so that the introduced fluorine amount corresponds to 95% by weight or more.

* * * * *

UNITED STATES PATENT AND TRADEMARK OFFICE
CERTIFICATE OF CORRECTION

PATENT NO. : 6,791,001 B2  
DATED : September 14, 2004  
INVENTOR(S) : Paolo Cuzzato et al.

Page 1 of 1

It is certified that error appears in the above-identified patent and that said Letters Patent is hereby corrected as shown below:

Column 5,
Line 18, "CEC" should read -- CFC --.
Line 22, "50° C. to 280° C." should read -- 50° C to 280° C --.
Line 38, "100° C." should read -- 100° C --.

Column 6,
Line 1, "50° C. to 183° C." should read -- 50° C to 183° C --
Line 16, "100° C." should read -- 100° C --.
Lines 28-29, "100° C. to 160° C." should read -- 100° C to 160° C --.
Line 33, "CEC" should read -- CFC --.

Signed and Sealed this

Fourteenth Day of December, 2004

JON W. DUDAS
*Director of the United States Patent and Trademark Office*